(12) United States Patent
Lincoln

(10) Patent No.: US 10,493,018 B1
(45) Date of Patent: Dec. 3, 2019

(54) TOPICAL MOISTURIZING COMPOSITION

(71) Applicant: Hemply Yours, LLC, Fort Worth, TX (US)

(72) Inventor: Kimberly M. Lincoln, Tucson, AZ (US)

(73) Assignee: Hemply Yours, LLC, Fort Worth, TX (US)

( * ) Notice: Subject to any disclaimer, the term of this patent is extended or adjusted under 35 U.S.C. 154(b) by 278 days.

(21) Appl. No.: 15/684,217

(22) Filed: Aug. 23, 2017

Related U.S. Application Data

(60) Provisional application No. 62/378,894, filed on Aug. 24, 2016.

(51) Int. Cl.
| | |
|---|---|
| A61K 36/18 | (2006.01) |
| A61K 8/92 | (2006.01) |
| A61Q 19/02 | (2006.01) |
| A61Q 19/08 | (2006.01) |
| A61Q 19/00 | (2006.01) |

(52) U.S. Cl.
CPC ............ *A61K 8/922* (2013.01); *A61Q 19/002* (2013.01); *A61Q 19/004* (2013.01); *A61Q 19/02* (2013.01); *A61Q 19/08* (2013.01)

(58) Field of Classification Search
CPC ...................................................... A61K 36/18
See application file for complete search history.

(56) References Cited

U.S. PATENT DOCUMENTS

| | | | |
|---|---|---|---|
| 2007/0280898 A1* | 12/2007 | Riddle ................. | A61K 8/4946 424/74 |
| 2008/0286390 A1 | 11/2008 | Tanyi | |

FOREIGN PATENT DOCUMENTS

| | | |
|---|---|---|
| WO | 2010072420 A2 | 7/2010 |

OTHER PUBLICATIONS

Booz, G. W.; Cannabidiol as an Emergent Therapeutic Strategy for Lessening the Impact of Inflammation on Oxidative Stress; Free Radical Biology Medicine, 51:1054-1061, 2011.
Abuzaytoun, R. et al.; Oxidative Stability of Flax and Hemp Oils; Journal of the American Oil Chemists's Society, vol. 83, No. 10, 855-861, 2006.
Burstein S.; Cannabidiol (CBD) and its analogs: a review of their effects on inflammation; Bioinorgainc and Medicinal Chemistry, 23:Abstract, Apr. 1, 2015.
Parry, J. et al.; Fatty Acid Composition and Antioxidant Properties of Cold-Pressed Marionberry, Boysenberry, Red Raspberry, and Blueberry seed oils; Journal of Agricultural Food and Chemistry, 53(3): Abstract, Feb. 9, 2005.
Oomah, D. B. et al.; Characteristics of hemp (*Cannabis sativa* L) seed oil; Food Chemistry, 76:33-43, 2002.
Nagarkatti, P. et al.; Cannabinoids as novel anti-inflammatory drugs; Future Medicinal Chemistry, 1(7):1333-1349, Oct. 2009.
Casanova, L M.; Inhibition of skin tumor growth and angiogenesis in vivo by activation of cannabinoid receptors; Journal of Clinical Investigation, 111:43-50, 2003.
Malfait, A. M. et al.; The nonpsychoactive cannabis constituent cannabidiol is an oral anti-arthritic therapeutic in murine collagen induced arthritis; Proceedings of the National Academy of Science, vol. 97, No. 17, 9561-9566, Aug. 15, 2000.
Kopcke, W.; Protection from Sunburn with β-Carotene—A Meta-analysis; Photochemistry and Photobiology, 84:284-288, 2008.
Ozcan, M. M. et al.; Chemical composition of carrot seeds (*Daucus carota* L.) cultivated in Turkey: characterization of the seed oil and essential oil; Grasas Y Aceites, 58(4):359-365, 2007.
Hakala, M. et al.; Evidence for the role of the oxygen-evolving manganese complex in photoinhibition of Photosystem II; Biochimica et. Biophysica Acta, 1706:68-80, 2005.
Stahl, W. et al.; β-Carotene and other carotenoids in protection from sunlight; American Journal of Clinical Nutrition, 96:1179S-1184S, 2012.
De Las Rivas, J. et al.; Two coupled β-carotene molecules protect P680 from photodamage in isolated Photosystem II reaction centres; Biochimica et. Biophysica Acta, 1142:155-164, 1993.
Leizer, C. et al.; The Composition of Hemp Seed Oil and Its Potential as an Important Source of Nutrition; Journal of Nutraceuticals, Functional & Medical Foods, vol. 2(4):35-53, 2000.
S. Montserrat-de la Paz., et al., Hemp (*Cannabis sativa* L.) Seed Oil: Analytical and Phytochemical Characterization of the Unsaponifiable Fraction; Journal of Agricultural and Food Chemistry, 62, 1105-1110, 2014.
Pereira de Melo, L. I., et al.; Pomegranate Seed Oil (*Punica granatum* L.): A Source of Punicic Acid (Conjugated α-Linolenic Acid); Journal of Human Nutrition and Food Science. 2(1):1024, Feb. 17, 2014.
Afaq, F., et al.; Protective effect of pomegranate-derived products on UVB-mediated damage in human reconstituted skin; Experimental Dermatology, 18:553-561, 2009.
Ganesan, P., et al; Current application of phytocompound-based nanocosmeceuticals for beauty and skin therapy; International Journal of Nanomedicine, 11:1987-2007, May 11, 2016.
Stander, S., et al; Distribution of cannabinoid receptor 1 (CB1) and 2 (CB2) on sensory nerve fibers and adnexal structures in human skin; Journal of Dermatological Science, 38(3), Abstract, Jun. 2005.

(Continued)

*Primary Examiner* — Rosanne Kosson
(74) *Attorney, Agent, or Firm* — Timmer Law Group, PLLC

(57) ABSTRACT

In a first aspect, there is provided a topical composition for moisturizing the skin, including a hemp seed oil from about 70 percent to about 85 percent; and a pomegranate seed oil from greater than zero to about 10 percent. In a second aspect, there is provided a topical composition for the body, including a hemp seed oil from about 70 percent to about 90 percent; a pomegranate seed oil from about 1 percent to about 10 percent; and an essential oil from about 1 percent to about 5 percent. In other aspects, there are methods for treating various physical conditions. In some aspects, there are topical compositions for hair, beard, after-shave, sunscreen, lip moisturizer, and insect repellant.

6 Claims, No Drawings

(56) References Cited

OTHER PUBLICATIONS

Scuderi, et al.; Cannabidiol in Medicine: A Review of its Therapeutic Potential in CNS Disorders; Phytotherapy Research, Res. 23, 597-602 (2009).

* cited by examiner

TOPICAL MOISTURIZING COMPOSITION

CROSS-REFERENCE TO RELATED APPLICATION

This application claims priority to U.S. Patent Application No. 62/378,894, filed Aug. 24, 2016, which is incorporated herein by reference in its entirety.

BACKGROUND

Technical Field

The present disclosure relates to a topical composition that may be used to treat, protect, and revitalize the lips, face, hands, hair, and body.

Description of Related Art

A person's skin can be negatively impacted by a number of factors, which includes diet, aging, disease, and environment. Ultraviolet (UV) radiation from the sun is a major damaging environmental factor that has serious adverse effects on the skin including, but no limited to, erythema, hyperpigmentation, premature aging. Solar UV radiation is formally divided into three categories: UVA (320-400 nm), UVB (280-320 nm), and UVC (100-280 nm) rays. Of these three categories, solar UVB radiation is the most damaging component of these solar radiation wavelengths. UVB radiation is absorbed mainly by the epidermal basal cell layer of the skin and once absorbed can initiate photo-oxidative damage to important biomolecules like DNA, protein, and lipids.

The benefits of hemp seed oil, and a *cannabis* oil, on the health of skin or as a remedy for dermatitis and other skin conditions, and to protect the skin from UV radiation damage, $1^{st}$-$3^{rd}$ degree skin burns, and insects is a highly unexplored area. Much of the focus on cannabinoid research is geared towards the neurochemical and neuroprotective effects of these compounds There is a need for an improved topical composition including at least one of an unrefined hemp seed oil and a *cannabis* oil that treats skin conditions including, but not limited to, preventing and reversing aging and the development of fine lines; hydrating dry and itchy; balancing oil production; enhancing pigmentation; reducing symptoms of redness (erythema) and inflammation associated with the skin conditions of acne, eczema and psoriasis; and reducing quantity of scar tissue.

SUMMARY

In a first aspect, there is provided a topical composition for moisturizing the skin, including a hemp seed oil from about 70 percent to about 85 percent; and a pomegranate seed oil from greater than zero to about 10 percent.

In an embodiment, the topical composition for moisturizing the skin includes a carrot seed oil from greater than zero to about 10 percent.

In one embodiment, the composition for moisturizing the skin includes a *cannabis* oil extract from about 1 percent to about 10 percent.

In another embodiment, the topical composition is used to treat a skin condition.

In some embodiments, the skin condition is at least one of the following: fine lines; wrinkles; inflammation; edema; age spots; depigmentation; skin texture; tone; roughness; photo damage; skin regeneration; environmental damage; smoothness; tightness; skin radiance; skin evenness; hyperpigmentation; dark spots; dark patches; skin brightness; photo-aged skin; intrinsically aged skin; extrinsically aged skin; abnormal skin cellular turnover; decreased skin barrier; decrease of skin's ability to retain moisture; blotchiness; redness; abnormal skin epidermal thickness; reduction of dermal epidermal junction; pore size; number of pores; and combinations thereof.

In still another embodiment, the topical composition administered to the skin of a patient achieves at least one of the following: rejuvenates sun damaged skin; rejuvenates aging skin; improves the appearance of fine lines; improves the appearance of wrinkles; promotes cell renewal; diminishes the appearance of age spots; diminishes the appearance of depigmentation; improves skin tone; improves texture; improves elasticity; reduces roughness; reduces photo damage; prevents environmental damage; plumps the skin; brightens the skin; lightens the skin; strengthens the ability of skin to regenerate itself; improves the appearance of age spots; lightens age spots; improves skin firmness; improves skin elasticity; improves skin resiliency; smooths the skin; tightens the skin; reduces the appearance of dark circles under the eye; improves lip texture; enhances natural lip color; increases lip volume; promotes epithelialization of post-procedure skin; restores the skin's barrier or moisture balance; improves the appearance of age spots; improves the appearance of skin pigmentation, and a combination thereof.

In an embodiment, there is a method of treating edema in a patient, including administering the topical composition to the skin of the patient in an amount effective to reduce the edema.

In a second aspect, there is provided a topical composition for the body, including a hemp seed oil from about 70 percent to about 90 percent; a pomegranate seed oil from about 1 percent to about 10 percent; and an essential oil from about 1 percent to about 5 percent.

In an embodiment, the topical composition for the body wherein the essential oil is from about 1 percent to about 3 percent.

In one embodiment, the topical composition for the body further includes a *cannabis* oil from about 1 percent to about 10 percent.

In yet another embodiment, the topical composition is used to treat edema in a patient.

In an embodiment, there is a method of treating edema in a patient, including administering the topical composition to the skin of a patient in an amount effective to reduce the edema. In some embodiments, the edema is abdominal edema. In a particular embodiment, the abdominal edema is adjacent to abdominal skin.

In a third aspect, there is provided a topical composition for hair on the face, including a hemp seed oil from about 40 percent to about 80 percent; a pomegranate seed oil from about 3 percent to about 40 percent; and an essential oil from about 1 to about 3 percent.

In an embodiment, the topical composition for hair on the face includes a carrot seed oil from an amount greater than zero to about 10 percent; and an avocado oil from about 1 percent to about 10 percent.

In one embodiment, the pomegranate seed oil is from about 3 percent to about 20 percent.

In a fourth aspect, there is provided a topical composition for use after shaving hair on the face, including a hemp seed oil from about 40 percent to about 80 percent; a pomegranate seed oil from about 1 percent to about 10 percent; a carrot seed oil from about 1 percent to about 10 percent; an essential oil from about 1 percent to about 3 percent; and a *cannabis* oil extract from about 1 percent to about 5 percent.

In a fifth aspect, there is provided a topical composition that repels insects, including a hemp seed oil from about 50 percent to about 80 percent.

In an embodiment, the topical composition that repels insects further includes a pomegranate seed oil from about greater than zero to about 10 percent.

In another embodiment, the topical composition that repels insects further includes an essential oil from about greater than zero to about 10 percent.

In a sixth aspect, there is provided a topical composition for sunscreen, including a hemp seed oil from about 50 percent to about 80 percent; a carotenoid from about 5 percent to about 10 percent; a beta-carotene from about 5 percent to about 10 percent; and a zinc oxide from about 1 percent to about 10 percent.

In an embodiment, the topical composition for sunscreen further includes a carrot seed oil from about greater than zero to about 10 percent.

In some embodiments, the topical composition for sunscreen further includes a pumpkin seed oil from about greater than zero to about 10 percent.

In a seventh aspect, there is provided a topical composition for a lip moisturizer, including a hemp seed oil from about 10 percent to about 20 percent; a pomegranate seed oil from about 70 percent to about 80 percent; and an essential oil from about 1 percent to about 5 percent.

In some embodiments, the topical composition for a lip moisturizer further includes a capsaicinoid from greater than zero to about 20 percent.

In an embodiment, the topical composition for a lip moisturizer further includes a *cannabis* oil extract from about 1 percent to about 10 percent.

Other aspects, features, and advantages will become apparent from the following detailed description when taken in conjunction with the accompanying drawings, which are a part of this disclosure and which illustrate, by way of example, principles of the inventions disclosed.

DESCRIPTION OF THE PREFERRED EMBODIMENT

It should be understood that although an illustrative implementation of one or more embodiments is provided below, the disclosed compositions and methods may be implemented using any number of techniques, whether currently known or in existence. The disclosure should in no way be limited to the illustrative implementations and techniques illustrated below, but may be modified within the scope of the appended claims along with their full scope of equivalents. All composition related percentages disclosed herein are by volume.

An embodiment provides a topical composition for moisturizing the skin, including hemp seed oil from about 70 percent to about 85 percent; and a pomegranate seed oil from greater than zero percent to about 10 percent by volume. In another embodiment, the topical composition includes pomegranate seed oil from about 5 percent to about 10 percent by volume. A further embodiment of the topical composition includes a carrot seed oil from greater than zero to about 10 percent by volume. In yet another embodiment, the topical composition includes a *cannabis* oil extract from greater than zero to about 10 percent by volume. In yet another embodiment, the topical composition includes a *cannabis* oil from about 1 percent to about 10 percent by volume. In an embodiment, the hemp seed oil, pomegranate seed oil, and carrot seed oil can be cold pressed unrefined oils.

The hemp seed oil is chemically composed of a blend of saturated and unsaturated fatty acids, plus a variety of natural products like carotenoids, tocopherols, cannabinoids, phytosterols, olefins and terpenes. The fatty acid content in unrefined hemp seed oil is much greater (75%) than the natural product content (25%). Hemp seed oil contains all of the essential amino acids and fatty acids required by the human body for maintaining proper nutrition. Hemp seed oil contains linoleic acid and alpha-linolenic acid as the major omega-6 and omega-3 polyunsaturated fatty acids in a ratio of 3:1, respectively, and is the main reason why this oil is recognized in the literature as a superior nutritional source to other seed oils. The unrefined hemp seed oil is produced using cold pressed extraction methods which includes controlling the temperature of the system (not to exceed 50 degrees Celsius) while pressing the hemp seeds. Unrefined hemp seed oil is fluorescent green yellow in color, with a slightly nutty flavor and smell. The hemp seed oil may be unrefined, cold pressed oil extracted from hemp seeds.

Cannabinoids interact with specific membrane-bound receptors in the body. A cannabinoid can have a preferred affinity for a cannabinoid receptor type 1 found primarily in the brain, hereinafter referred to as "$CB_1$ cannabinoids." In another example, a cannabinoid can have a preferred affinity for a cannabinoid receptor type 2 found primarily in the immune system with the greatest density in the spleen, herein after referred to as "$CB_2$ cannabinoids."

Unrefined hemp seed oil contains trace amounts or less than 0.05% by volume of a non-psychoactive cannabinoid, which can be in one example, but not for limitation, a cannabidiol (CBD). Unrefined hemp seed oil contains psychoactive delta-9-tetrahydrocannabinol (THC) in concentrations no greater than 50 ppm. CBD has a greater affinity for the $CB_2$ receptors than the $CB_1$ receptors.

In some embodiments, the *cannabis* oil included in the composition can be a *cannabis* oil extract. In an exemplary embodiment, the *cannabis* oil extract can be extracted from *cannabis* flowers using carrier oils like, hemp seed oil, pomegranate seed oil, or flax seed oil as the solvent. In some embodiments, the hemp seed oil may be a microwave treated oil. In another exemplary embodiment, the *cannabis* oil extract may be unrefined and extracted from preheated *cannabis* flower using carrier oils. The chemical composition of the *cannabis* oil extract can include at least one of the following: omega fatty acids, chlorophyll, terpenes, cannabigerol, cannabidiol, tetrahydrocannbinol, and phytosterols.

In some embodiments, the *cannabis* oil can include at least one of the following: tetrahydrocannabinol, cannabidiol, cannabinol, cannabigerol-type compounds, cannabigerol, cannabichromene, cannabicyclol, cannabivarin, tetrahydrocannabivarin, cannabidivarin, cannabichromevarin, cannabigerovarin, cannabigerol monomethyl ether, *cannabis* terpenes, *cannabis* phytosterols and *cannabis* phytopigments.

An embodiment provides a topical composition with a *cannabis* oil in an amount greater than that found in unrefined hemp seed oil. In another embodiment, the topical composition includes from about 1 percent to about 10 percent of an unrefined *cannabis* oil extract. An embodiment provides a method of manufacturing a topical composition for treating a skin condition including providing an oil, adding a *cannabis* oil extract into the oil, and mixing the oil and the *cannabis* oil extract.

An embodiment provides a topical composition with a *cannabis* oil extract in an amount greater than that found in unrefined hemp seed oil. In another embodiment, the topical composition includes from about 1 percent to about 10 percent of an unrefined *cannabis* oil extract. An embodiment provides a method of manufacturing a topical composition for treating a skin condition including providing an unrefined hemp seed oil, adding a *cannabis* oil extract to the unrefined hemp seed oil, and mixing the unrefined hemp seed oil and the *cannabis* oil extract.

Pomegranate seed oil may be unrefined, cold pressed extracted from pomegranate seeds, or refined. The oil can be light yellow or soft amber with a slightly fruity odor in unrefined form or clear and odorless in the refined form. The unsaturated fatty acids of pucinic acid will be present in 70-80% in the unrefined oil form. The chemical composition of pomegranate oil may include: saturated fatty acids, unsaturated fatty acids, cannabinoids, terpenes, and phytosterols.

Carrot seed oil may be unrefined, cold pressed extracted from carrot seed. The oil can be golden-to-dark green with a sweet earthy smell in unrefined form. The chemical composition of carrot seed oil may include: saturated fatty acids and unsaturated fatty acids, cannabinoids, terpenes, phytosterols, carotenoids, and essential oils.

Essential oils can include at least one of, but not limited to, cardamom, coriander, tea tree, lemon, spearmint, peppermint, sandalwood, lavender, chamomile, basil, lemon thyme, lavender, *eucalyptus*, citronella, and black cumin oil, cardamom oil, and coriander oil. An embodiment provides that the concentration of any individual essential oil will not exceed 3 percent of the total chemical formulation.

In another embodiment, there is provided a topical composition for the body such as, but not limited to, a massage oil including a hemp seed oil from about 70 percent to about 90 percent, a pomegranate seed oil from about 1 percent to about 10 percent; and an essential oil from about 1 percent to about 5 percent by volume. An embodiment of the topical composition can include the essential oil from about 1 percent to about 3 percent by volume. In yet another embodiment, the topical composition includes a *cannabis* oil extract from about 1 percent to about 10 percent by volume. In another embodiment, the topical composition includes at least one of cardamom, coriander, lavender, chamomile, peppermint, spearmint and sandalwood.

In one embodiment, a topical composition for hair on the face or head such as, but not limited to, facial hair care, a hemp seed oil from about 50 percent to about 80 percent; a pomegranate seed oil from about 3 percent to about 40 percent; and an essential oil from about 1 to about 3 percent. In some embodiments, the topical composition for hair on the face or head includes a carrot seed oil from an amount greater than zero to about 10 percent and an avocado oil from about 1 to 10 percent. In an embodiment, the pomegranate seed oil is from about 3 to about 20 percent of the topical composition for hair on the face or head. In an embodiment, the topical composition for hair on the face or head includes a hemp seed oil from about 70 percent to about 80 percent; a pomegranate seed oil from about 3 percent to about 10 percent; a carrot seed oil from about 0 percent to about 10 percent; and an avocado oil from about 0 to about 10 percent; and an essential oil from about 1 to about 3 percent by volume. In another embodiment, the topical composition for hair on the face or includes a hemp seed oil from about 50 percent to about 80 percent and a pomegranate seed oil from about 20 percent to about 40 percent. Another embodiment provides that the topical composition includes at least one of cardamom, coriander, lavender, sandalwood, rosemary, spearmint, and peppermint.

In another embodiment, a topical composition for use after shaving hair on the face, legs or arms, includes a hemp seed oil from about 40 percent to about 80 percent; a pomegranate seed oil from about 1 percent to about 10 percent; a carrot seed oil from about 1 percent to about 10 percent; and an essential oil from about 1 percent to about 3 percent by volume, and a *cannabis* oil extract from 1 percent to about 5 percent Another embodiment of the topical composition includes from hemp seed oil from about 80 percent to about 90 percent.

In yet another embodiment, a topical composition that repels insects includes: hemp seed oil from about 50 percent to about 80 percent by volume. An embodiment of the topical composition includes pomegranate seed oil from about greater than zero to about 10 percent by volume. In still another embodiment, the topical composition includes an essential oil from about greater than zero to about 10 percent by volume. In a further embodiment, the topical composition includes an essential oil from about greater than zero to about 5 percent by volume.

In one embodiment, the topical composition for sunscreen includes: a hemp seed oil from about 50 percent to about 80 percent; a carotenoid from about 5 percent to about 10 percent; a beta-carotene from about 5 percent to about 10 percent; and a zinc oxide from about 1 percent to about 10 percent by volume. In a further embodiment, the topical composition includes a zinc oxide from about 2 percent to about 3 percent by volume. Another embodiment includes carrot seed oil from about greater than zero to about 10 percent in the topical composition. In yet another embodiment, the topical composition includes a pumpkin seed oil from about greater than zero to about 10 percent by volume.

An embodiment of a topical composition for a lip moisturizer includes: a hemp seed oil from about 10 percent to about 20 percent; a pomegranate seed oil from about 70 percent to about 80 percent; and an essential oil from about 1 percent to about 5 percent. In a further embodiment, the topical composition includes capsaicinoid from about greater than zero to about 20 percent by volume. In another embodiment, the topical composition includes capsaicinoid from about 1 percent to about 3 percent by volume. In yet another embodiment, the topical composition includes a *cannabis* oil extract from about 1 percent to about 10 percent.

In another embodiment, the composition includes terpenes. An embodiment includes terpenes from about 1 percent to about 5 percent of the total volume of the topical composition. An embodiment of the topical composition includes terpenes from about 1 percent to about 3 percent.

Any of the topical compositions described herein can be used to treat a skin condition. The skin condition can be at least one of the following: fine lines and wrinkles; age spots and depigmentation; decreased skin texture; tone and elasticity; roughness and photo damage; decreased ability of skin to regenerate itself; environmental damage; decreased smoothness and tightness of skin; age spots; fine and coarse lines and wrinkles; fine and coarse periocular wrinkles; nasolabial folds; facial fine and coarse lines; decreased skin radiance and evenness; decreased skin firmness; hyperpigmentation; dark spots; dark patches; decreased skin brightness and youthful appearance; photo-aged skin; intrinsically and extrinsically aged skin; abnormal skin cellular turnover; decreased skin barrier; decrease of skin's ability to retain moisture; brown and red blotchiness; redness; abnormal skin epidermal thickness; reduction of dermal epidermal junction; increased pore size and number of pores; and a combination thereof.

Another embodiment provides that the topical composition administered to the skin of a patient achieves at least one of the following results: rejuvenates sun damaged and aging skin; improves the appearance of fine lines and wrinkles; promotes cell renewal; diminishes the appearance of age spots and depigmentation; improves skin tone, texture and elasticity; reduces roughness and photo damage; prevents or reduces environmental damage; plumps the skin; brightens the skin; lightens the skin; strengthens the ability of skin to regenerate itself; improves the appearance of age spots; brightens and lightens age spots; improves skin firmness, elasticity, resiliency; smooths, tightens, or fills in fine lines on the skin; reduces the appearance of dark circles under the eye; improves lip texture or condition; enhances natural lip color; increases lip volume; promotes epithelialization of post-procedure skin; restores the skin's barrier or moisture balance; improves the appearance of age spots; improves the appearance of skin pigmentation, and a combination thereof.

Another embodiment includes treating bursitis and sore or tight muscles by massaging the topical composition into the skin.

Another embodiment includes use as topical to protect the fading of color in tattoos and dyed hair upon exposure to sunlight.

An embodiment includes the prevention or treatment of stretch marks induced from pregnancy or weight gain.

In yet another embodiment, a method provides for treating a condition with the topical composition, where the method includes topical application of the topical composition to treat a skin condition including, but not limited to, preventing and reversing aging and the development of fine lines; hydrating dry and itchy; balancing oil production; enhancing pigmentation; reducing symptoms of redness (erythema) and inflammation associated with the skin conditions of rosacea, eczema and psoriasis; and reducing generation of scar tissue, acne, and healing lacerations or open wounds.

An embodiment includes a pharmaceutical kit comprising a chemotherapeutic agent and a topical composition described herein.

A pharmaceutical kit including a topical composition described herein.

Another embodiment includes a method of manufacturing a topical sunscreen composition including adding at least one of hemp seed oil and a *cannabis* oil extract. Compounds that absorb UV radiation within the specified wavelengths of the UV radiation categories function as a means to prevent direct radiative damage to important biomolecules, which is induced by sunlight exposure and absorption. The UV-Vis spectrum of hemp seed oil shows absorbance in both the UVB and UVC ranges and can surprisingly serve as a broad spectrum UV protectant.

In one exemplary embodiment, topically administering about 1 mL of a topical composition described herein twice daily to skin with uneven and blotchy skin pigmentation for a period of 6 weeks including a hemp seed oil from about 60 percent to about 85 percent and a pomegranate seed oil from about 1 percent to about 10 percent, and a carrot seed oil from 1 percent to about 10 percent to skin of a patient resulted in the enhancement and evening of skin pigmentation.

Another embodiment provides a method of manufacturing a topical composition by adding treated hemp seed oil to the topical composition. The hemp seed oil can be treated by various methods to improve the skin treatment or protectant properties of the oil; for example, and not limitation, hemp seed oil can be treated by drying, heat, microwave, steam, autoclave, electrification, vibrations, sound, light, and/or centrifugation. Surprisingly, the treated hemp seed oil can include improved concentration and/or quality of active constituents: essential omega-3 and omega-6 fatty acids, beta-carotene, tocopherols, a cannabinoid, terpenes, and phytosterols. In some embodiments, the hemp seed oil can be used to extract a *cannabis* oil extract.

In an embodiment, there is a method of treating edema of a patient, including administering the topical composition described herein to the skin of the patient in an amount effective to reduce edema. In one embodiment, the method can include treating abdominal edema of a patient, including administering the topical composition described herein to the patient in an amount effective to reduce abdominal edema. In an embodiment, the step of administering can include applying the topical composition to the abdominal area of the patient. In an embodiment, the topical composition is applied to the abdominal skin of a patient to reduce edema in the affected area (e.g., areas adjacent to the abdominal skin of the patient). In still another embodiment, the step of administering comprises applying a topical composition described herein to the face of a patient in an amount effective to reduce edema (e.g., undereye bags and other areas affected by swelling).

In one exemplary embodiment, topically administering about one tablespoon of a topical composition including a hemp seed oil from about 60 percent to about 85 percent, a pomegranate seed oil from about 1 percent to about 10 percent, and a carrot seed oil from about 1 percent to 10 percent to skin of a patient in the abdominal area resulted in a reduction of edema in the abdominal area of about 0.5-1.5 inches after about 1-4 hours.

The topical compositions and methods described herein can advantageously provide at least one of the following benefits: protect the fading of color in tattoos and dyed hair upon exposure and for the prevention or treatment and stretch marks induced from pregnancy and weight gain.

At least one embodiment is disclosed and variations, combinations, and/or modifications of the embodiment(s) and/or features of the embodiment(s) made by a person having ordinary skill in the art within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes 2, 3, 4, etc.; greater than 0.10 includes 0.11, 0.12, 0.13, etc.). For example, whenever a numerical range with a lower limit, $R_l$, and an upper, $R_u$, is disclosed, any number falling within the range is specifically disclosed. In particular, the following numbers within the range are specifically disclosed: $R=R_l+P_k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Unless otherwise stated, the term "about" shall mean plus or minus 5 percent of the subsequent value. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrow terms such as consisting of, consisting essentially of, and comprised substantially of. Accordingly, the scope of protection is not limited by the description set out above but is defined by the claims that follow, the scope including all equivalents of the subject matter of the claims. Every claim is incorporated as further disclosure into the specification and the claims are embodiment(s) of the present invention.

What is claimed is:

1. A topical composition for moisturizing the skin, comprising:
    a hemp seed oil in a therapeutically effective amount from about 70 percent to about 85 percent; and a pomegranate seed oil in a therapeutically effective amount from greater than zero to about 10 percent.

2. The topical composition according to claim 1, further comprising:
    a carrot seed oil from greater than zero to about 10 percent.

3. The topical composition according to claim 1, further comprising:
    a *cannabis* oil extract from about 1 percent to about 10 percent.

4. The topical composition according to claim 1, wherein the topical composition is used to treat a skin pigmentation condition.

5. The topical composition of claim 4, wherein the skin pigmentation condition is one or more conditions selected from the group consisting of inflammation; age spots; depigmentation; skin evenness; hyperpigmentation; dark spots; dark patches; skin brightness; blotchiness; and redness.

6. The topical composition of claim 4, wherein the topical composition administered to the skin of a patient achieves one or more results selected from the group consisting of: diminished appearance of age spots; diminished appearance of depigmentation; improved skin tone; brightened skin; lightened skin; improved appearance of age spots; lightened age spots; reduced appearance of dark circles under the eye; and improved appearance of skin pigmentation.

* * * * *